United States Patent [19]
Henrick et al.

[11] 3,975,429
[45] Aug. 17, 1976

[54] CYCLOPROPANEMETHYL ESTERS OF CINNAMIC ACID AND DERIVATIVES THEREOF

[75] Inventors: Clive A. Henrick; Gerardus B. Staal, both of Palo Alto, Calif.

[73] Assignee: Zoecon Corporation, Palo Alto, Calif.

[22] Filed: Sept. 15, 1975

[21] Appl. No.: 613,395

Related U.S. Application Data

[60] Division of Ser. No. 412,806, Nov. 5, 1973, Pat. No. 3,928,413, which is a continuation-in-part of Ser. No. 350,708, April 13, 1973, Pat. No. 3,923,871, which is a continuation-in-part of Ser. No. 263,902, June 19, 1972, abandoned, which is a continuation-in-part of Ser. No. 255,368, May 22, 1972, abandoned.

[52] U.S. Cl. .......................... 260/473 R; 260/473 F
[51] Int. Cl.$^2$ ......................... C07C 69/76
[58] Field of Search .................... 260/473 R, 473 F

[56] References Cited
OTHER PUBLICATIONS

Kaiser et al., J. Org. Chem. 1970 35(4) pp. 1198–1199.
Chemical Abs. vol. 72, 121138w (1970).

*Primary Examiner*—Paul J. Killos
*Attorney, Agent, or Firm*—Donald W. Erickson

[57] ABSTRACT

Organic esters and thioesters characterized by the presence of a cyclopropane moiety, synthesis thereof, and compositions thereof for the control of mites and ticks.

12 Claims, No Drawings

CYCLOPROPANEMETHYL ESTERS OF CINNAMIC ACID AND DERIVATIVES THEREOF

This is a division of Ser. No. 412,806, filed Nov. 5, 1973 now U.S. Pat. No. 3,928,413 which is a continuation-in-part of Ser. No. 350,708, filed Apr. 13, 1973, now U.S. Pat. No. 3,923,871 which is a continuation-in-part of Ser. No. 263,902, filed June 19, 1972, now abandoned, which is a continuation-in-part of Ser. No. 255,368, filed May 22, 1972, now abandoned.

This invention relates to novel compounds, synthesis thereof, compositions thereof, and the control of mites and ticks.

The compounds of the present invention are effective for the control of mites and especially spider mites. Spider mites are plant feeders and cause serious damage to orchard trees, field crops, greenhouse plants and other vegetation. They feed on the foliage of fruit of plants and trees and attack a variety of plants and trees due to their wide distribution. Spider mites of the family Tetranychidae, such as *Tetranychus urticae, Tetranychus canadensis, Tetranychus cinnabarinus, Tetranychus pacificus, Bryobia praetiosa, Oligonychus pratensis, Oligonychus ilicis, Panonychus citri, Panonychus ulmi*, and similar relates species, are of particular biological interest and economic importance. Other mites are those of the family Tarsonemidae, such as *Steneotarsonemus pallidus*.

Compounds of the present invention of the following formulas A and B are effective control agents for spider mites.

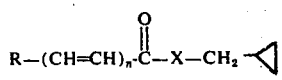  (A)

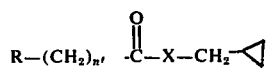  (B)

where,

X is oxygen or sulfur;

R is phenyl, naphthyl or cycloalkyl, each optionally substituted by one or more halogen, alkyl, alkoxy, aralkoxy, aryl or aryloxy groups;

$n$ is one or two; and $n'$ is zero or a positive integer from one to 10.

Hereinafter, each of R, X, $n$ and $n'$ is as defined above unless otherwise specified.

Preferred compounds within this class are those wherein the R group is phenyl or naphthyl and one of the substituents on the R group is in the para-position relative to the acid group attached to the ring. Preferred substituents are alkyl of one to 10 carbon atoms, alkoxy of one to 10 carbon atoms, phenyl, phenylalkyl of seven to ten carbon atoms, phenylalkoxy of seven to 10 carbon atoms, chlorine or bromine.

Especially preferred are those compounds where $n$ is one or $n'$ is zero, one or two, and the R group is phenyl and is substituted in the para-position by methyl, octyl, phenyl, benzyl, methoxy, phenoxy, octyloxy, benzyloxy, or chloro.

The compounds of formula A or B are applied to the mite at any stage, namely during the egg, larvae, nymphal or adult stages in view of their effect in causing inhibition of egg hatching abnormal development leading to death, inability to pass from one stage to the next, or inability to reproduce. Some of the compounds also exhibit a residual ovicidal effect. A compound of formula A or B or mixtures thereof, can be applied at dosage levels of the order of 0.001% to 1%. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compounds is employed, although a higher concentration of the active compound can be used depending on the type of application apparatus. The formulations can include emulsifying agents and wetting agents to assist in the application and effectiveness of the ingredient.

The esters and thioesters of this invention are prepared by conventional esterification methods, for example by reacting an acid halide of the formula

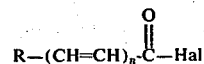

or

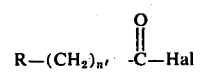

with cyclopropanemethyl alcohol or cyclopropanemethyl mercaptan with or without added pyridine to obtain the corresponding ester or thioester. The reaction may be carried out neat or in an organic solvent inert to the reaction, such as a hydrocarbon or ether solvent. Usually an excess of the alcohol or mercaptan is employed and the reaction proceeds at room temperature satisfactorily, although higher or lower temperatures may be used.

Alternatively, the esters may be prepared by transesterification of a corresponding alkyl ester with the lithium salt of cyclopropanemethyl alcohol, or esterification with cyclopropanemethyl alcohol and acid catalyst, in an inert solvent.

Cyclopropanemethyl alcohol can be prepared as described by Sarel and Newman, *J. Am. Chem. Soc.* 78, 5416 (1956); Sneen et al, ibid, 83, 4843 (1961); Siegel and Bergstron, ibid 72, 3815 (1950) and 74, 145 (1952); U.S. Pat. Nos. 2,294,084 and 3,074,984; and references cited therein.

The term "alkyl", as used herein, refers to a straight or branched chain saturated aliphatic hydrocarbon group of one to 15 carbon atoms, e.g., methyl, ethyl, propyl, i-propyl, n-butyl, s-butyl, t-butyl, pentyl, hexyl, heptyl, n-octyl, 2-methyloctyl, nonyl, decyl, undecyl, 2-methylundecyl, 6-methylundecyl, dodecyl, pentadecyl and the like. The term "lower alkyl" refers to an alkyl group of one to six carbon atoms.

The term "alkoxy", as used herein, refers to a straight or branched chain saturated aliphatic hydrocarbonoxy group of one to 15 carbon atoms, e.g., methoxy, ethoxy, n-propoxy, i-propoxy, n-butoxy, i-butoxy, t-butoxy, n-heptyloxy, n-dodecyloxy, 2-methyloctyloxy, and the like.

The term "cycloalkyl", as used herein, refers to a monovalent cycloalkyl moiety of four to eight carbon atoms, i.e. cyclobutyl, cyclopentyl, cyclohexyl, cycloheptyl, and cyclooctyl.

The term "aryl", as used herein, refers to a monovalent aromatic hydrocarbon group containing from six to 14 carbon atoms such as phenyl, tolyl, xylyl, mesityl, naphthyl, ethylphenyl, t-butylphenyl, isopropylphenyl, chlorophenyl, and methoxyphenyl.

The term "aralkyl", as used herein, refers to a monovalent hydrocarbon group containing from seven to 15 carbon atoms in which a hydrogen atom of an alkyl group having a chain length of one to six carbon atoms is substituted by an aryl group, such as benzyl, phenethyl, methylbenzyl, naphthylmethyl and naphthylethyl.

The terms "aryloxy" and "aralkyloxy", as used herein, refer to the groups aryl-O- and aralkyl-O- where aryl and aralkyl are as defined above.

The term "halogen", as used herein, refers to fluorine, chlorine and bromine.

The esters of the present invention are useful for the control of mites and ticks which are ectoparasitic on animals and birds. The esters can be applied in either solution or in powder (dust) form in a conventional manner.

The following examples are provided to illustrate the syntheses of the compounds of the present invention and the practice of the present invention. Temperature is reported in degrees Centigrade.

EXAMPLE 1

To a mixture of 3.46 g. of anhydrous sodium hydrosulfide and 14 ml. dimethylformamide is added with cooling 4.0 g. of cyclopropanemethyl chloride. After standing 2 hours at room temprature, water and ether are added, the aqueous phase separated and extracted with ether, and the combined organic phases washed with brine, dried over calcium sulfate, filtered and distilled to yield cyclopropanemethyl mercaptan, boiling at 97°–98° at 1 atm.

EXAMPLE 2

To a solution of 3.05 g. of trans-cinnamic acid in dry benzene is added 5 ml of oxalyl chloride. The reaction mixture is stirred at room temperature, under nitrogen, for 2 hours. Solvent is removed in vacuo and replaced by fresh dry benzene and 3.9 ml. of cyclopropanemethyl alcohol is added. The reaction mixture is stirred overnight at room temperature, under nitrogen. The reaction is worked up by washing with water and brine, drying over calcium sulfate and evaporating under reduced pressure and fractionally distilling to yield the cyclopropanemethyl ester of trans-cinnamic acid, (cyclopropanemethyl trans-cinnamate) b.p. 100° (bath) at .1 mm.

EXAMPLE 3

To a solution of 3.5 g. of p-methylcinnamic acid and 2.4 ml. of thionyl chloride in dry ether is added 0.5 ml. dry dimethylformamide. The reaction mixture is stirred at room temperature for 6 days. The top layer of the bisphasic mixture is decanted and the volatile material is removed by evaporating under reduced pressure. The residue is taken up in dry ether and 2.34 g. of cyclopropanemethyl alcohol is added followed, at 0°, by 5.2 ml. of dry pyridine. The reaction mixture is stirred at room temperature for 1 day. The reaction is worked up by addition of water, ether and pentane, separating the organic layer, and then washing with sulfuric acid, potassium carbonate, water and brine. The solution is dried over calcium sulfate and evaporated under reduced pressure and fractionally distilled to yield the cyclopropanemethyl p-methylcinnamate, b.p. (bath) 95°–100° (0.01 mm).

Following the procedure of this example, the acids of Column I are converted to the corresponding acid chloride and then reacted with cyclopropylmethyl alcohol to yield the esters of Column II.

I p-chlorocinnamic acid
p-methoxycinnamic acid
p-benzylcinnamic acid
p-benzyloxycinnamic acid
4-(benzyloxy)-3,5-dimethoxycinnamic acid
m-bromocinnamic acid
p-bromocinnamic acid
p-butoxycinnamic acid
4-butoxy-3-fluorocinnamic acid
p-chlorocinnamic acid
3-chloro-4-methoxycinnamic acid
2-chloro-5-methylcinnamic acid
p-(dodecyloxy)cinnamic acid
p-ethoxycinnamic acid
p-ethylcinnamic acid
m-fluorocinnamic acid
p-(isohexyloxy)cinnamic acid
p-isopropoxycinnamic acid
p-isopropylcinnamic acid
o-methoxycinnamic acid
p-(p-methylphenethyl)cinnamic acid
p-(octyloxy)cinnamic acid
p-phenoxycinnamic acid
p-phenylcinnamic acid
2,4,5-trimethoxycinnamic acid
p-octylcinnamic acid
5-(p-chlorophenyl)valeric acid
5-(phenyl)valeric acid
5-(p-octylphenyl)valeric acid
5-(p-octyloxyphenyl)valeric acid
5-(p-methoxy)valeric acid
5-(p-methyl)valeric acid
2-naphthylacetic acid

II cyclopropanemethyl p-chlorocinnamate
cyclopropanemethyl p-methoxycinnamate
cyclopropanemethyl p-benzylcinnamate
cyclopropanemethyl p-benzyloxycinnamate
cyclopropanemethyl 4-(benzyloxy)-3,5-dimethoxycinnamate
cyclopropanemethyl m-bromocinnamate
cyclopropanemethyl p-butoxycinnamate
cyclopropanemethyl 4-butoxy-3-fluorocinnamate
cyclopropanemethyl p-chlorocinnamate
cyclopropanemethyl 3-chloro-4-methoxycinnamate
cyclopropanemethyl 2-chloro-5-methylcinnamate
cyclopropanemethyl p-(dodecyloxy)cinnamate
cyclopropanemethyl p-ethoxycinnate
cyclopropanemethyl p-ethylcinnamate
cyclopropanemethyl m-fluorocinnamate
cyclopropanemethyl p-(isohexyloxy)cinnamate
cyclopropanemethyl p-isopropoxycinnamate
cyclopropanemethyl p-isopropylcinnamate
cyclopropanemethyl o-methoxycinnamate
cyclopropanemethyl p-(p-methylphenethyl)cinnamate
cyclopropanemethyl p-(octyloxy)cinnamate cyclopropanemethyl p-phenoxycinnamate
cyclopropanemethyl p-phenylcinnamate
cyclopropanemethyl 2,4,5-trimethoxycinnamate
cyclopropanemethyl p-octylcinnamate
cyclopropanemethyl 5-(p-chlorophenyl)valerate
cyclopropanemethyl 5-(phenyl)valerate
cyclopropanemethyl 5-(p-octylphenyl)valerate
cyclopropanemethyl 5-(p-octyloxyphenyl)valerate
cyclopropanemethyl 5-(p-methoxy)valerate
cyclopropanemethyl 5-(p-methyl)valerate
cyclopropanemethyl 2-naphthylacetate

EXAMPLE 4

To a solution of 17.08 ml. of n-butyl lithium in hexane, under nitrogen, at 0°–5° is added dropwise 1.965 g. of cyclopropyl-methyl alcohol. The reaction mixture is stirred for one-half hour at room temperature and then the hexane is evaporated under reduced pressure. Dry tetrahydrofuran is added to the residue, forming an orange-yellow slurry. To this slurry is slowly added, as a solution in tetrahydrofuran, 2.36 g. of octyl p-(octyloxy)-cinnamate [prepared from p-hydroxycinnamic acid and excess octyliodide in the presence of potassium carbonate and dimethylformamide]. The reaction mixture is stirred at room temperature overnight. The resultant brown solution is worked up by adding water and extracting with ether, washing the ether layer with water and brine, drying over calcium sulfate, filtering, and evaporating under reduced pressure. The resultant product is separated by preparative thin-layer chromatography to yield 0.65 g. of cyclopropanemethyl p-(octyloxy) cinnamate, m.p. 36°–37.5°.

EXAMPLE 5

To a solution of 0.35 g. of p-octylbenzoic acid and 0.035 ml. dimethylformamide in dry ether is added, at 8°, 0.161 ml. of thionyl chloride. The reaction mixture is stirred for 2 hours at room temperature and then cooled to 10°C. To this stirred mixture, under nitrogen, is then added 0.140 g. of cyclopropylmethyl alcohol. The addition of 0.18 ml. of pyridine yields an immediate white precipitate. After stirring overnight at room temperature, the reaction is worked up by adding water and ether, acidifying, extracting with ether, adding sodium bicarbonate until slightly basic, washing with water, copper sulfate, water and brine, drying over calcium sulfate, filtering, drying and then separating the product, cyclopropylmethyl ester of 4-octylbenzoate, b.p. (bath) 113° (0.03 mm).

Using the above procedure, the esters of Column IV are prepared from the acids of Column III.

III benzoic acid
2,4-dichlorobenzoic acid
4-phenylbenzoic acid
4-methoxybenzoic acid
4-ethylbenzoic acid
1-naphthoic acid
2-naphthylacetic acid
4(benzyloxy)benzoic acid
2-naphthoic acid
4-(5-methoxynaphthyl)butyric acid
4-octyloxybenzoic acid
4-phenoxybenzoic acid
4-methylbenzoic acid
4-chlorobenzoic acid
3-(2,4-dichlorophenyl)propionic acid
7-(3,5-dimethoxyphenyl)heptanoic acid
8-(4-octylphenyl)octanoic acid

IV cyclopropanemethyl benzoate
cyclopropanemethyl 2,4-dichlorobenzoate
cyclopropanemethyl 4-phenylbenzoate
cyclopropanemethyl 4-methoxybenzoate
cyclopropanemethyl 4-ethylbenzoate
cyclopropanemethyl 1-naphthoate
cyclopropanemethyl 2-naphthylacetate
cyclopropanemethyl 4(benzyloxy)benzoate
cyclopropanemethyl 2-naphthoate
cyclopropanemethyl 4-(5-methoxynaphthyl)butyrate
cyclopropanemethyl 4-octyloxybenzoate
cyclopropanemethyl 4-phenoxybenzoate
cyclopropanemethyl 4-methylbenzoate
cyclopropanemethyl 4-chlorobenzoate
cyclopropanemethyl 3-(2,4-dichlorophenyl)propionate
cyclopropanemethyl 7-(3,5-dimethoxyphenyl)heptanoate
cyclopropanemethyl 8-(4-octylphenyl)octanoate Following the procedure of Example 3, the acids of Column V are converted to the corresponding acid chloride and esterified with cyclopropanemethyl alcohol to yield the compounds of Column VI.

V 5-phenyl-2,4-pentadienoic acid
5-(4-biphenylyl)-2,4-pentadienoic acid
5-(o-methoxyphenyl)-2,4-pentadienoic acid
5-(p-methoxyphenyl)-2,4-pentadienoic acid
5-(1-naphthyl)-2,4-pentadienoic acid
5-(m-chlorophenyl)-2,4-pentadienoic acid
5-(3,4-dichlorophenyl)-2,4-pentadienoic acid
5-(2,6-dichlorophenyl)-2,4-pentadienoic acid
5-(p-bromophenyl)-2,4-pentadienoic acid
5-(p-chlorophenyl)-2,4-pentadienoic acid
5-(2-naphthyl)-2,4-pentadienoic acid
5-(3,4-dimethoxyphenyl)-2,4-pentadienoic acid

VI cyclopropanemethyl 5-phenyl-2,4-pentadienoate
cyclopropanemethyl 5-(4-biphenylyl)-2,4-pentadienoate
cyclopropanemethyl 5-(o-methoxyphenyl)-2,4-pentadienoate
cyclopropanemethyl 5-(p-methoxyphenyl)-2,4-pentadienoate
cyclopropanemethyl 5-(1-naphthyl)-2,4-pentadienoate
cyclopropanemethyl 5-(m-chlorophenyl)-2,4-pentadienoate
cyclopropanemethyl 5-(3,4-dichlorophenyl)-2,4-pentadienoate
cyclopropanemethyl 5-(2,6-dichlorophenyl)-2,4-pentadienoate
cyclopropanemethyl 5-(p-bromophenyl)-2,4-pentadienoate
cyclopropanemethyl 5-(p-chlorophenyl)-2,4-pentadienoate
cyclopropanemethyl 5-(2-naphthyl)-2,4-pentadienoate
cyclopropanemethyl 5-(3,4-dimethoxyphenyl)-2,4-pentadienoate Those compounds where R is cycloalkyl are prepared by treating the appropriate cycloalkane carboxaldehyde with an equimolar amount of triethyl phosphonoacetate in dimethyl formamide solution with a slight molar excess of sodium hydroxide. The reaction is carried out under nitrogen and at from 20° to reflux. The resultant ethyl ester of the 3-cycloalkane acrylic acid can be directly treated with about a 4.5 molar excess of lithium cyclopropanemethyl alcoholate in tetrahydrofuan to yield the desired cyclopropanemethyl ester. It is, however, preferred to treat the ethyl cycloalkaneacrylate with aqueous sodium hydroxide and methanol to obtain the free acid which is then esterified according to the procedure of Example 3. Using this preferred method, the acids of Column VII are converted to the esters of Column VIII.

VII 3-cyclohexaneacrylic acid
3-cyclobutaneacrylic acid
3-cyclopentaneacrylic acid
3-cycloheptaneacrylic acid
3-cyclooctaneacrylic acid
3-(4-methoxycyclohexane)acrylic acid
3-(4-chlorocyclohexane)acrylic acid
3-(4-octyloxycyclohexane)acrylic acid
3-(4-methylcyclohexane)acrylic acid

VIII cyclopropanemethyl 3-cyclohexaneacrylate
cyclopropanemethyl 3-cyclobutaneacrylate
cyclopropanemethyl 3-cyclopentaneacrylate
cyclopropanemethyl 3-cycloheptaneacrylate
cyclopropanemethyl 3-cyclooctaneacrylate
cyclopropanemethyl 3-(4-methoxycyclohexane)acrylate
cyclopropanemethyl 3-(4-chlorocyclohexane)acrylate
cyclopropanemethyl 3-(4-octyloxycyclohexane)acrylate
cyclopropanemethyl 3-(4-methylcyclohexane)acrylate Thioesters are prepared by treating a solution of the corresponding acid in benzene with oxalyl chloride, heating for 1 to 8 hours and then removing the benzene solvent. To this concentrate is added a molar excess of the cyclopropanemethyl mercaptan, prepared in Example 1, in ether, followed by the addition of 0° of pyridine. The reaction mixture is stirred at room temperature and then refluxed for from 1 to 5 days and the product separated by pouring the mixture into water, adding ether, separating the organic phase, washing with aqueous sodium bicarbonate and brine, drying over calcium sulfate and removing the solvent.

In the above manner, the acids of Column I and of Example 2 are converted to the thio esters of Column IX.

IX

S-(cyclopropanemethyl) p-chlorocinnamthioate
S-(cyclopropanemethyl) p-methoxycinnamthioate
S-(cyclopropanemethyl) p-benzylcinnamthioate
S-(cyclopropanemethyl) p-benzyloxycinnamthioate
S-(cyclopropanemethyl) 4-(benzyloxy)-3,5-dimethoxycinnamthioate
S-(cyclopropanemethyl) m-bromocinnamate
S-(cyclopropanemethyl) p-bromocinnamate
S-(cyclopropanemethyl) p-butoxycinnamate
S-(cyclopropanemethyl) 4-butoxy-3-fluorocinnamate
S-(cyclopropanemethyl) p-chlorocinnamate
S-(cyclopropanemethyl) 3-chloro-4-methoxycinnamate
S-(cyclopropanemethyl) 2-chloro-5-methylcinnamate
S-(cyclopropanemethyl) p-(dodecyloxy)cinnamate
S-(cyclopropanemethyl) p-ethoxycinnamate
S-(cyclopropanemethyl) p-ethylcinnamate
S-(cyclopropanemethyl) m-fluorocinnamate
S-(cyclopropanemethyl) p-(isohexyloxy)cinnamate
S-(cyclopropanemethyl) p-isopropoxycinnamate
S-(cyclopropanemethyl) p-isopropylcinnamate
S-(cyclopropanemethyl) o-methoxycinnamate
S-(cyclopropanemethyl) p-(p-methylphenethyl)cinnamate
S-(cyclopropanemethyl) p-(octyloxy)cinnamate
S-(cyclopropanemethyl) p-phenoxycinnamthioate
S-(cyclopropanemethyl) p-phenylcinnamate
S-(cyclopropanemethyl) 2,4,5-trimethoxycinnamate
S-cyclopropanemethylcinnamate The mite control agents of the present invention can be used alone in an inert agriculturally acceptable carrier substance for the control of mites (Arachnids) or can be used in mixture with insecticides and/or juvenile hormone analogs known in the art to provide a broader spectrum of activity.

The effectiveness of the compounds of the present invention is demonstrated below.

Adults (*Tetranychus urticae*) are allowed to oviposit for 24 hours on castor bean leaf discs (1 cm.) on moist cottonwool.

After 24 hours, the adults are removed and the leaf discs are then dipped in acetone solutions of cyclopropanemethyl p-chlorocinnamate and of cyclopropanemethyl p-octylbenzoate at 0.1%.

After submersion for 1 second, the solvent on the leaf discs is allowed to dry and the leaf discs are then glued to a plastic petri dish to prevent crumpling.

Six days later (when all the eggs on untreated discs have emerged), the number of unhatched eggs is calculated as a percentage of the total number originally present, corrected for any spontaneous non-emergence observed in control discs treated only with solvent (Abbott correction).

Both cyclopropanemethyl p-chlorocinnamate and cyclopropanemethyl p-octylbenzoate at the above concentration prevent the hatching of 100% of the eggs.

A wettable powder suitable for field application after dilution can be formulated by blending and then airmilling a mixture of 20 to 30% of an ester of this invention, 60 to 70% of a solid carrier such as Attaclay X-250, 1 to 3% of an anionic surfactant, such as Igepon T-77, and 3 to 5% of a dispersing agent such as Marasperse N-22.

The wettable powder is applied, after dilution with water, using ultra-low volume sprayers. Dilutions containing the ester within a concentration range of about 0.01% to 10% are generally employed.

We claim as our invention:

1. A compound of formula A or B

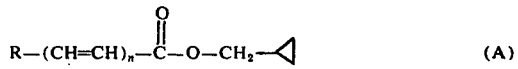

(A)

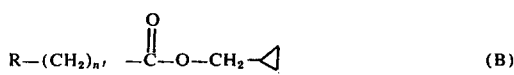

(B)

wherein,
$n$ is one or two;
$n'$ is zero or a positive integer from one to 10; and R is phenyl or naphthyl, each substituted by one or more of alkoxy, aralkoxy or aryloxy.

2. A compound according to claim 1 of the formula:

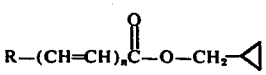

wherein n is one or two and R is phenyl or naphthyl, each substituted by alkoxy of one or 10 carbon atoms or phenylalkoxy of seven to 10 carbon atoms.

3. A compound according to claim 1 of the formula

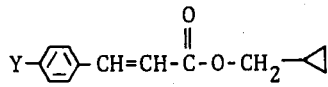

wherein Y is methoxy, octyloxy, benzyloxy or phenoxy.

4. The compound, cyclopropanemethyl p-methoxycinnamate, according to claim 3.

5. The compound, cyclopropanemethyl p-octyloxycinnamate, according to claim 3.

6. The compound, cyclopropanemethyl p-benzyloxycinnamate, according to claim 3.

7. The compound, cyclopropanemethyl p-ethoxycinnamate, according to claim 1.

8. The compound, cyclopropanemethyl p-isopropoxycinnamate, according to claim 1.

9. The compound, cyclopropanemethyl 2,4,5-trimethoxycinnamate, according to claim 1.

10. A compound according to claim 1 of the formula:

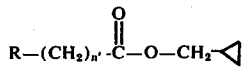

wherein $n'$ is zero or a positive integer from one to 10 and R is phenyl or naphthyl, each substituted by alkoxy of one to 10 carbon atoms or phenylalkoxy of seven to 10 carbon atoms.

11. A compound according to claim 1 of the formula:

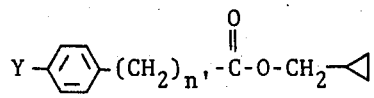

wherein $n'$ is zero, one or two and Y is methoxy, octyloxy, phenoxy or benzyloxy.

12. The compound, cyclopropanemethyl 4-benzyloxybenzoate, according to claim 11.

* * * * *

UNITED STATES PATENT OFFICE
CERTIFICATE OF CORRECTION

Patent No. 3,975,429            Dated August 16, 1976

Inventor(s) Clive A. Henrick; Gerardus B. Staal

It is certified that error appears in the above-identified patent and that said Letters Patent are hereby corrected as shown below:

Claim 2, line 3, "one or 10" should read --one to 10--.

Signed and Sealed this

Thirtieth Day of November 1976

[SEAL]

Attest:

RUTH C. MASON
Attesting Officer

C. MARSHALL DANN
Commissioner of Patents and Trademarks